(12) United States Patent
Kelley et al.

(10) Patent No.: US 6,730,107 B2
(45) Date of Patent: May 4, 2004

(54) SINGLE LUMEN RAPID-EXCHANGE CATHETER

(75) Inventors: Gregory S. Kelley, San Diego, CA (US); Herbert R. Radisch, Jr., San Diego, CA (US); Show-Mean Wu, San Diego, CA (US)

(73) Assignee: SciMed Life Systems, Inc., Maple Grove, MN (US)

( * ) Notice: Subject to any disclaimer, the term of this patent is extended or adjusted under 35 U.S.C. 154(b) by 220 days.

(21) Appl. No.: 09/938,008

(22) Filed: Aug. 23, 2001

(65) Prior Publication Data

US 2003/0040769 A1 Feb. 27, 2003

(51) Int. Cl.[7] .............................................. A61M 29/00
(52) U.S. Cl. ................... 606/192; 606/194; 604/103.04
(58) Field of Search ...................... 604/103.04; 606/194

(56) References Cited

U.S. PATENT DOCUMENTS

| | | | |
|---|---|---|---|
| 4,323,071 A | | 4/1982 | Simpson |
| 4,516,972 A | | 5/1985 | Samson |
| 5,135,494 A | * | 8/1992 | Engelson et al. ......... 604/99.02 |
| 5,209,728 A | * | 5/1993 | Kraus et al. ............. 604/96.01 |
| 5,364,354 A | * | 11/1994 | Walker et al. ........... 604/103.1 |
| 5,454,788 A | * | 10/1995 | Walker et al. ........... 604/99.04 |
| 5,490,837 A | * | 2/1996 | Blaeser et al. ......... 604/103.11 |
| 5,516,336 A | | 5/1996 | McInnes |
| 5,947,927 A | * | 9/1999 | Mertens ................. 604/164.13 |
| 5,951,568 A | | 9/1999 | Schatz |
| 6,090,126 A | * | 7/2000 | Burns ......................... 606/194 |

OTHER PUBLICATIONS

Reduction in Ischemec Vascular Complications With a Hydrophilic–Coated Intra–Aortic Balloon Catheter; Winters, Smith, Cohen, Kopistansky, and McBride; Catheterization and Cardiovascular Interventions 46:357–362 (1999).*
Usefulness of Hydrophilic Coating on Arterial Sheath Introducer in Transradial Coronary Intervention; Saito, Tanaka, Hiroe, Miyashita, Takahashi, Satake, Tanaka, and Yamamoto; Catheterization and Cardiovascular Interventions 56:328–332 (2002).*

* cited by examiner

Primary Examiner—Michael J. Milano
Assistant Examiner—Bradford C Pantuck
(74) Attorney, Agent, or Firm—Nydegger & Associates

(57) ABSTRACT

A single lumen rapid-exchange catheter includes a distal sealing port and a proximal sealing port both dimensioned for receiving a guidewire to establish a fluid-tight seal therewith. Each tubular shaped sealing port has a length, and a diameter, and is made of a hydrophilic polymer. In operation, the guidewire is inserted through the distal sealing port and exits from the catheter tube at the shoulder of the catheter tube and through the proximal sealing port. When fluid is present, each sealing port will enlarge to establish a fluid-tight seal with the guidewire. A diverter can be disposed at the proximal sealing port to redirect the guidewire from the lumen and out of the catheter tube through the proximal sealing port.

5 Claims, 2 Drawing Sheets

SINGLE LUMEN RAPID-EXCHANGE CATHETER

FIELD OF THE INVENTION

The present invention pertains generally to catheters and methods for using such catheters. More particularly, the present invention pertains to rapid-exchange catheters. The present invention pertains particularly, though not exclusively, to single lumen rapid-exchange catheters.

BACKGROUND OF THE INVENTION

During the performance of an interventional procedure, such as a percutaneous transluminal coronary angioplasty procedure, it is often necessary to exchange one catheter for another. For instance, after one catheter has been used to make an initial diagnosis, it may be necessary to remove the diagnostic catheter and replace it with a surgical catheter. Also, the sequential use of different surgical catheters may be required. During intervention, for example in an angioplasty procedure, lesions of the same vessel often require treatment with different size balloons. This requires that angioplasty balloon catheters having different size balloons be exchanged. Further, after a procedure has been completed, it may be desirable to reintroduce the diagnostic catheter to assess the progress that has been made. Still further, at the end of the treatment, it also may be desirable to introduce a drug delivery catheter to perfuse the lesion with agents that will inhibit or prevent a restenosis. Suffice it to say, during an interventional procedure in the vasculature, there are several occasions when it may be necessary or desirable to exchange catheters.

There are essentially two types of catheters that cooperate with guidewires for use in placement of the catheter in the vasculature of a patient. The first type of catheter is an "over-the-wire" catheter in which a guidewire lumen extends the full length of the catheter shaft. This type of catheter requires that the guidewire be sufficiently long for its proximal end to remain in place until the distal end of the catheter has been withdrawn from the patient. The second type of catheter is the so-called "rapid-exchange" catheter in which the guidewire lumen does not extend the full length of the catheter shaft. Instead, the guidewire exits the catheter shaft at the distal end of the catheter, and at some point between the distal end and the proximal end of the catheter which is preferably closer to the distal end. Thus, when positioned in the vasculature, most of the guidewire extends externally in a proximal direction alongside the catheter shaft. This limits the interaction between the guidewire, and reduces the necessary extracorporeal length of the guidewire in comparison to the guidewire length required by the over-the wire catheters.

Rapid-exchange catheters typically have multiple separate lumens with one lumen dedicated as a guidewire lumen which can be used for the exchange of catheters. One example of such a rapid-exchange, multi-lumen catheter is disclosed in U.S. Pat. No. 5,346,505 which issued to Leopold for an invention entitled "Easily Exchangeable Catheter System." Such a catheter has a guidewire lumen and an inflation lumen formed in the catheter body.

In any case, the present invention recognizes that rapid-exchange catheters having several lumens will typically have large cross-sectional areas. This is most likely undesirable because, in order to minimize trauma to a patient, it is desirable to make the smallest possible puncture in a patient's body. Consequently, a catheter should have the smallest possible cross-sectional area.

In light of the above, and in a departure from the known art, it is the object of the present invention to provide a multi-purpose, single lumen rapid-exchange catheter that uses the same lumen for receiving a guidewire and for establishing fluid communication through the catheter. Another object of the present invention is to provide a rapid-exchange catheter having sealing ports that provide for a smooth and easy insertion and withdrawal of a guidewire therefrom without compromising the fluid communication function of the catheter. Yet another object of the present invention is to provide a rapid-exchange catheter which is relatively simple to manufacture, easy to use, and comparatively cost effective.

SUMMARY OF THE PREFERRED EMBODIMENTS

The present invention is directed to a single lumen rapid-exchange catheter. For the present invention, the rapid-exchange catheter includes a catheter tube having a single lumen which is suitable for dual purposes. First, the lumen is used to establish a fluid communication channel through the catheter. Second, the lumen is dimensioned for also receiving a guidewire. To do this, the catheter tube of the present invention includes a distal sealing port and a proximal sealing port which are formed into the catheter tube. Structurally, each of the sealing ports is tubular shaped and has a length and a diameter. Specifically, the length of each sealing port needs to be long enough to establish a substantially fluid-tight seal with the guidewire. The diameter of each sealing port, however, needs to be slightly greater than the diameter of the guidewire in order to allow the guidewire to pass through the sealing port. More specifically, when the guidewire is in a sealing port, there will be a distance between the diameter of the sealing port and the diameter of the guidewire that varies within a range between zero and approximately two thousandths of an inch (0 to 0.002 inches). Despite the fact this distance exists, it is still necessary that the port establish a substantially fluid-tight seal with the guidewire. The material that is used for the sealing port is important in this aspect.

As intended for the present invention, each sealing port preferably incorporates a hydrophilic polymer. Specifically, each sealing port preferably has an inner lining that extends along the length of the sealing port and that is made of a hydrophilic polymer. Consequently, upon exposure to a fluid, the hydrophilic material in the sealing ports become lubricious, and allow for the guidewire to slide through the sealing ports. Moreover, when fluid is present, each sealing port swells up against the guidewire to establish a substantially fluid-tight seal with the guidewire.

As envisioned by the present invention, in a catheter exchange, one catheter will be withdrawn from the vasculature, while the guidewire remains in situ. Thus, the subsequent engagement of a sequential catheter will first require insertion of the proximal end of the guidewire through the distal sealing port of the catheter and then the passing of the guidewire out of the proximal sealing port. To do this, there are a couple of features envisioned for the present invention. First, a diverter having a lip is disposed inside the lumen at the proximal sealing port of the catheter tube. The lip of the diverter extends radially into the lumen of the catheter tube to redirect the guidewire from inside the catheter tube through the proximal sealing port. Specifically, the diverter extends into the lumen of the catheter tube approximately one-half the diameter of the catheter tube. Secondly, the rapid-exchange catheter of the present invention can be formed with a shoulder which demarcates a proximal portion of the rapid-exchange catheter from a distal portion of the rapid-exchange catheter. More specifically, the shoulder causes a longitudinal axis for the proximal portion of the rapid-exchange catheter to be off-set from, and substantially parallel to, the longitudinal axis of the distal portion of the rapid-exchange catheter. The proximal sealing port is then located on the catheter tube at the shoulder in alignment with the longitudinal axis of the distal portion of the catheter tube. With this configuration for the catheter tube, a guidewire can be received through the proximal sealing port and the distal portion of the catheter tube without there being any significant bending of the guidewire.

In the operation of the present invention, a guidewire is first advanced into the vasculature of a patient. The proximal end of the guidewire is then inserted through the distal sealing port of the present invention extending through the lumen of the catheter tube, and through the balloon. The guidewire exits the catheter tube through the proximal sealing port of the present invention. The rapid-exchange catheter of the present invention is then advanced over the guidewire and into the vasculature of the patient.

When the rapid-exchange catheter has reached its desired position in the patient's body, the balloon can be inflated to a desired pressure, such as eighteen atmospheres of pressure. Meanwhile, the guidewire remains in the catheter tube during balloon inflation. Since fluid is used to inflate the balloon, each sealing port, in contact with fluid, swells up against the guidewire and establishes a substantially fluid-tight seal with the guidewire. It is important to also note that due to the nature of hydrophilic material, each sealing port is highly lubricious when wet. Thus, wet hydrophilic material allows the guidewire to move easily through the sealing ports. Accordingly, the rapid-exchange catheter of the present invention can be removed from the patient's body by withdrawing the rapid-exchange catheter over the guidewire while the guidewire remains in place in the patient.

BRIEF DESCRIPTION OF THE DRAWINGS

The novel features of this invention, as well as the invention itself, both as to its structure and its operation, will be best understood from the accompanying drawings, taken in conjunction with the accompanying description, in which similar reference characters refer to similar parts, and in which.

DESCRIPTION OF THE PREFERRED EMBODIMENT

Figure 1:
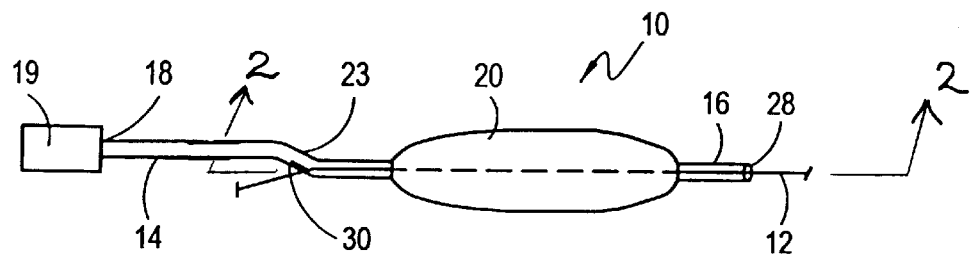
FIG. 1 is a perspective view of a rapid-exchange catheter of the present invention.

Referring initially to FIG. 1, a rapid-exchange catheter in accordance with this present invention is shown and is generally designated 10. As shown, the rapid-exchange catheter 10 of the present invention is engaged with a guidewire 12. The rapid-exchange catheter 10 includes a catheter tube 14 having a distal end 16 and a proximal end 18. A fluid source 19 is attached to the proximal end 18 of the catheter tube 14. As also shown in FIG. 1, a balloon 20 is mounted near the distal end 16 of the catheter tube 14 and is in fluid communication with the catheter tube 14. For the present invention, balloon 20 is preferably made of any suitable angioplasty balloon material, such as polyethylene terephthalate or polyurethane.

Figure 2:
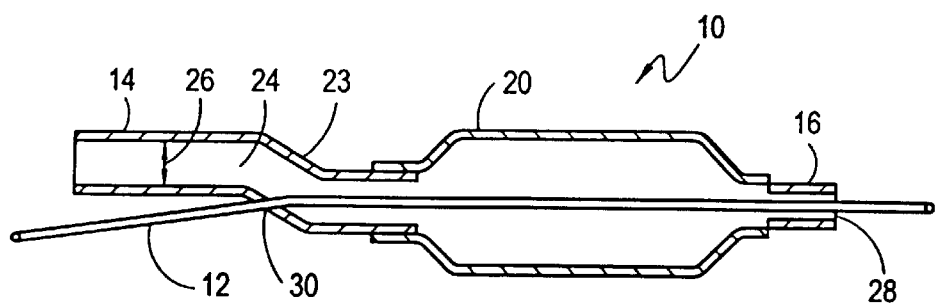
FIG. 2 is a longitudinal cross-sectional view of the present invention as seen along the line 2—2 in FIG. 1.

As shown in FIGS. 1 and 2, the rapid-exchange catheter 10 is engaged with a guidewire 12. Specifically, the guidewire 12 having a diameter 22 (see FIG. 3) that extends partially through the catheter tube 14, and completely through the balloon 20. As shown in FIG. 2, the catheter tube 14 of the present invention is formed with a shoulder 23 which demarcates a proximal portion of the rapid-exchange catheter 10 from a distal portion of the rapid-exchange catheter 10. More specifically, the shoulder 23 causes a longitudinal axis for the proximal portion of the rapid-exchange catheter 10 to be off-set from, and substantially parallel to, the longitudinal axis of the distal portion of the rapid-exchange catheter 10. Additionally, the catheter tube 14 has a single lumen 24 having a diameter 26. The diameter 26 of the catheter tube 14 is large enough to allow for fluid communication through the lumen 24 and to also allow the guidewire 12 to pass through the lumen 24 of the catheter tube 14. Stated differently, the diameter 26 of the catheter tube 14 is greater than the diameter 22 of the guidewire 12.

Importantly, the catheter tube 14 of the present invention is formed with a distal sealing port 28 and a proximal sealing port 30. The distal sealing port 28 is formed on the catheter tube 14 proximal to the distal end 16 of the catheter tube 14. The proximal sealing port 30 is formed on the catheter tube 14 distal to the proximal end 18 of the catheter tube 14. More specifically, the proximal sealing port 30 is formed at the shoulder 23 of the catheter tube 14 in alignment with the longitudinal axis of the distal portion of the catheter tube 14. Balloon 20 is mounted on the catheter tube 14 between the distal sealing port 28 and the proximal sealing port 30. The sealing ports 28 and 30 of the present invention can perhaps be best seen in FIG. 1.

Figure 3:
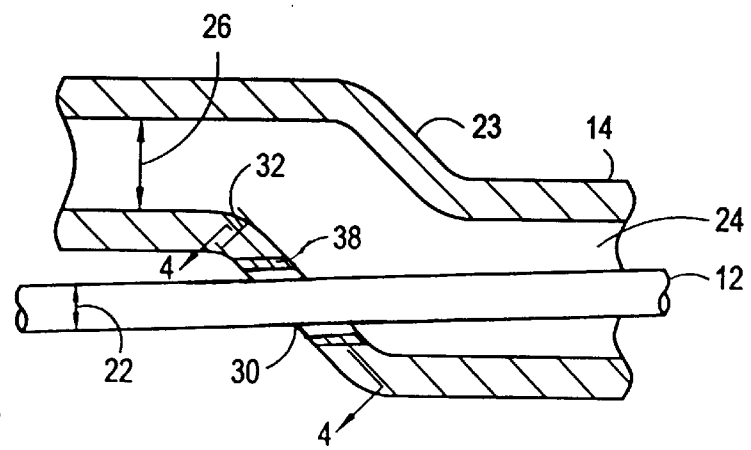
FIG. 3 is a cross-sectional view of the proximal sealing port of the present invention with a guidewire passing through the port.

FIG. 3 is a cross-sectional view of the proximal sealing port 30 of the present invention. For purposes of this disclosure, it is to be appreciated that both the distal sealing port 28 and the proximal sealing port 30 have essentially the same structural characteristics. With this in mind, both the distal sealing port 28 and the proximal sealing port 30 are dimensioned with a length 32 and a diameter 34 for receiving the guidewire 12, and for establishing a substantially fluid-tight seal with the guidewire 12.

Figure 4:
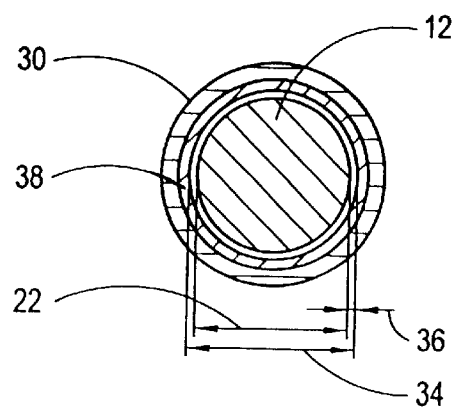
FIG. 4 is a cross-sectional view of the proximal sealing port as would be seen along the line 4—4 in FIG. 3 with a complete catheter.

The diameter 34 (See FIG. 4) of the proximal sealing port 30 is slightly larger than the diameter 22 of the guidewire 12. More specifically, when the guidewire 12 is inserted into the proximal sealing port 30, there is a distance 36 between the guidewire diameter 22 and the sealing port diameter 34 that can best be appreciated with reference to FIG. 4. For purposes of the present invention, the distance 36 varies within a range between zero and approximately two thousandths of an inch (0–0.002 inches).

Importantly, the sealing ports 28 and 30 of the present invention are preferably made with a hydrophilic polymer. As shown in FIG. 3, the proximal sealing port 30 can have an inner lining 38, which is preferably made of a hydrophilic polymer, that extends along its length 32. When in contact with a fluid, the hydrophilic proximal sealing port 30 is lubricious to allow the guidewire 12 to slide through the proximal sealing port 30. Moreover, when fluid is present, proximal sealing port 30 swells up to establish a substantially fluid-tight seal with the guidewire 12. At this time, the proximal sealing port 30 is substantially in contact with the guidewire 12. Stated differently, the distance 36 between the guidewire 12 and the proximal sealing port 30 is approximately zero.

Figure 5:
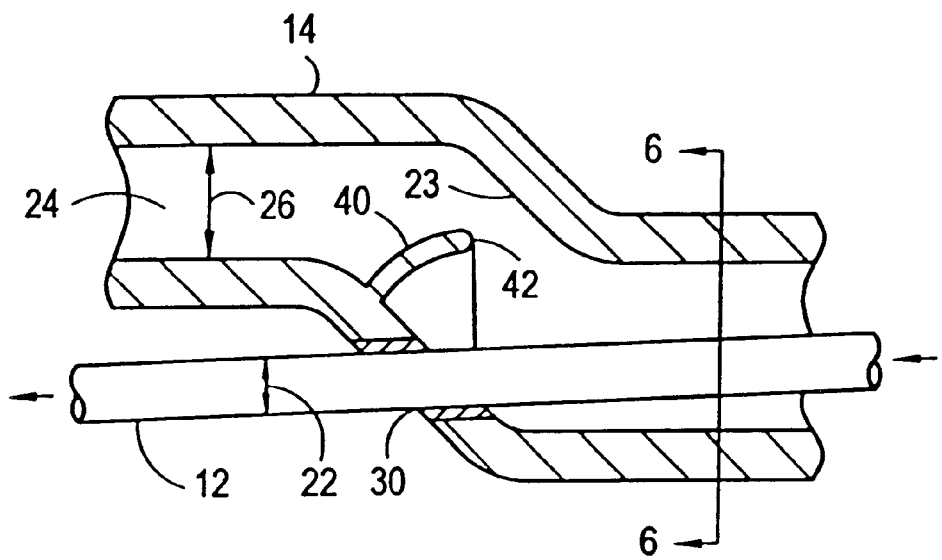
FIG. 5 is an exploded view of an alternate embodiment of the proximal sealing port as shown in FIG. 3.
Figure 6:
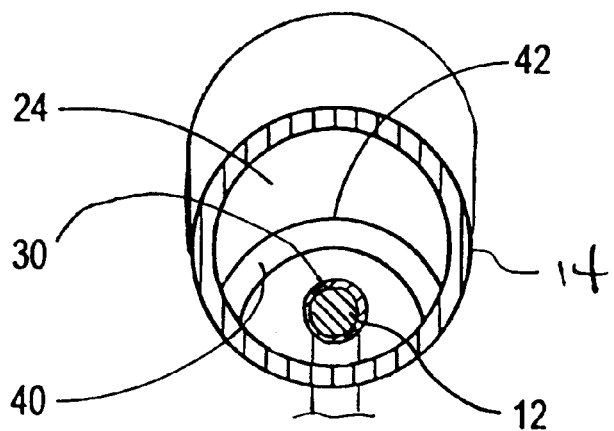
FIG. 6 is a cross-sectional view of the alternate embodiment as would be seen along the line 6—6 in FIG. 5.

FIG. 5 shows an alternate embodiment of the rapid-exchange catheter 10 of the present invention wherein a diverter 40 is disposed at the proximal sealing port 30. Specifically, the diverter 40 is dimensioned for redirecting the guidewire 12 from inside lumen 24 and into the proximal sealing port 30. For this purpose, the diverter 40 has a lip 42 that extends radially into the lumen 24 of the catheter tube 14, approximately one-half the diameter 26 of the catheter tube 14. As shown in FIG. 6, the lip 42 of the diverter 40 also extends substantially across the width of the lumen 24 so that as the guidewire 12 is advanced proximally through the lumen 24 it can be easily engaged by the diverter 40 and directed through the proximal sealing port 30.

OPERATION

In the operation of the present invention, guidewire 12 is first advanced into the vasculature of a patient. The proximal end of the guidewire 12 is then inserted through the distal sealing port 28 of the present invention extending through the lumen 24 of the catheter tube 14, and through the balloon 20. The guidewire 12 exits the catheter tube 14 at the shoulder 23 of the catheter tube 14 and through the proximal sealing port 30 of the present invention, without any significant bending of the guidewire 12. The rapid-exchange catheter 10 of the present invention is then advanced over the guidewire 12 and into the vasculature of the patient.

When the rapid-exchange catheter 10 of the present invention reaches a desired position in the patient's body, the balloon 20 can be inflated at a desired pressure, such as eighteen atmosphere of pressure. Meanwhile, the guidewire 12 remains in the catheter tube 14 during balloon inflation. As each sealing port 28 and 30 comes into contact with a fluid, it swells up and comes into direct contact with guidewire 12. Consequently, each sealing port 28 and 30 establishes a substantially fluid-tight seal with the guidewire 12. Contact with fluid also increases the lubricity of the sealing ports 28 and 30. Consequently, relative movement between the catheter 10 and the guidewire 12 is facilitated for any repositioning of the catheter 10 or removal of the catheter 10 from the vasculature.

While the particular Single Lumen Rapid-Exchange Catheter as herein shown and disclosed in detail is fully capable of obtaining the objects and providing the advantages herein before stated, it is to be understood that it is merely illustrative of the presently preferred embodiments of the invention and that no limitations are intended to the details of construction or design herein shown other than as described in the appended claims.

What is claimed is:

1. A rapid-exchange catheter system which comprises:

a guidewire having a diameter;

a catheter tube formed with a lumen and having a distal end and a proximal end;

a distal sealing port having a length and formed into said catheter tube in fluid communication with said lumen, said sealing port having an inner liner positioned substantially along said length thereof, with said inner liner being made of a hydrophilic polymer material and dimensioned for receiving said guidewire therethrough to establish a substantially fluid-tight seal therewith;

a proximal sealing port having a length and formed into said catheter tube in fluid communication with said lumen, said sealing port having an inner liner positioned substantially along said length thereof, with said inner liner being made of a hydrophilic polymer material and dimensioned for receiving said guidewire therethrough to establish a substantially fluid-tight seal therewith, and wherein said distal sealing port and said proximal sealing port each has a respective diameter for receiving said guidewire with a distance therebetween, and further wherein said distance between said diameter of said guidewire and respective said diameters of said distal sealing port and said proximal sealing port varies within a range between zero and approximately two thousandths of an inch (0–0.002 inches); and a balloon connected in fluid communication with said lumen of said catheter tube between said proximal sealing port and said distal sealing port, with said guidewire extending between said distal sealing port and said proximal sealing port and through said balloon when said guidewire is engaged with said catheter tube.

2. A rapid-exchange catheter system as recited in claim 1 further comprising a diverter disposed at said proximal sealing port of said catheter tube and dimensioned for redirecting said guidewire therethrough.

3. A rapid-exchange catheter system as recited in claim 2 wherein said catheter tube has a lumen with a diameter and said diverter has a lip, with said lip of said diverter extending radially into said lumen of said catheter tube approximately one-half said diameter of said catheter tube to redirect said guidewire from inside said lumen of said catheter tube through said proximal sealing port.

4. A rapid-exchange catheter system as recited in claim 1 wherein said balloon is inflated to a pressure of eighteen atmospheres and further wherein said catheter tube is formed with a shoulder.

5. A rapid-exchange catheter system as recited in claim 1 further comprising a fluid source attached to said proximal end of said catheter tube in fluid communication with said balloon.

* * * * *